(12) United States Patent
Warner

(10) Patent No.: US 6,276,364 B1
(45) Date of Patent: Aug. 21, 2001

(54) PROTECTIVE SLEEVE FOR A CHRONICALLY IMPLANTED INTRAVENOUS SITE

(76) Inventor: Sheryl A. Warner, 1063 Raintree La., Palm Beach Gardens, FL (US) 33410

( * ) Notice: Subject to any disclaimer, the term of this patent is extended or adjusted under 35 U.S.C. 154(b) by 0 days.

(21) Appl. No.: 09/294,731

(22) Filed: Apr. 19, 1999

Related U.S. Application Data

(63) Continuation of application No. 08/756,330, filed on Nov. 26, 1996, now abandoned.

(51) Int. Cl.[7] ........................................................ A61F 13/00
(52) U.S. Cl. .............................. 128/846; 128/878; 602/3
(58) Field of Search ...................................... 128/846, 878, 128/879, 880, 882; 602/3, 5; 2/2, 16, 22, 59, 240

(56) References Cited

U.S. PATENT DOCUMENTS

| | | | |
|---|---|---|---|
| 3,416,518 | * 12/1968 | Samuels | 602/3 |
| 5,143,762 | * 9/1992 | Ho | 128/846 |
| 5,228,851 | * 7/1993 | Burton | 604/171 |
| 5,592,953 | * 1/1997 | Delao | 602/3 |

* cited by examiner

*Primary Examiner*—Michael A. Brown
(74) *Attorney, Agent, or Firm*—Norman Friedland

(57) ABSTRACT

The present invention relates to a protective sleeve for a chronically-implanted intravenous (IV) site. The sleeve is made of a prophylactic waterproof material, and is normally worn by a person while showering to prevent moisture from invading the IV site. The sleeve in one embodiment has two elastomeric beads which form a watertight seal between a person's arm and the beads, and the sleeve billows in its mid-section so that it does not snag the catheter. The sleeve in another embodiment has a binding at one end and at least a binding at the other end integrally formed in the sleeve or in another embodiment a plurality of indentations axially spaced on a tapered portion of the sleeve.

11 Claims, 2 Drawing Sheets

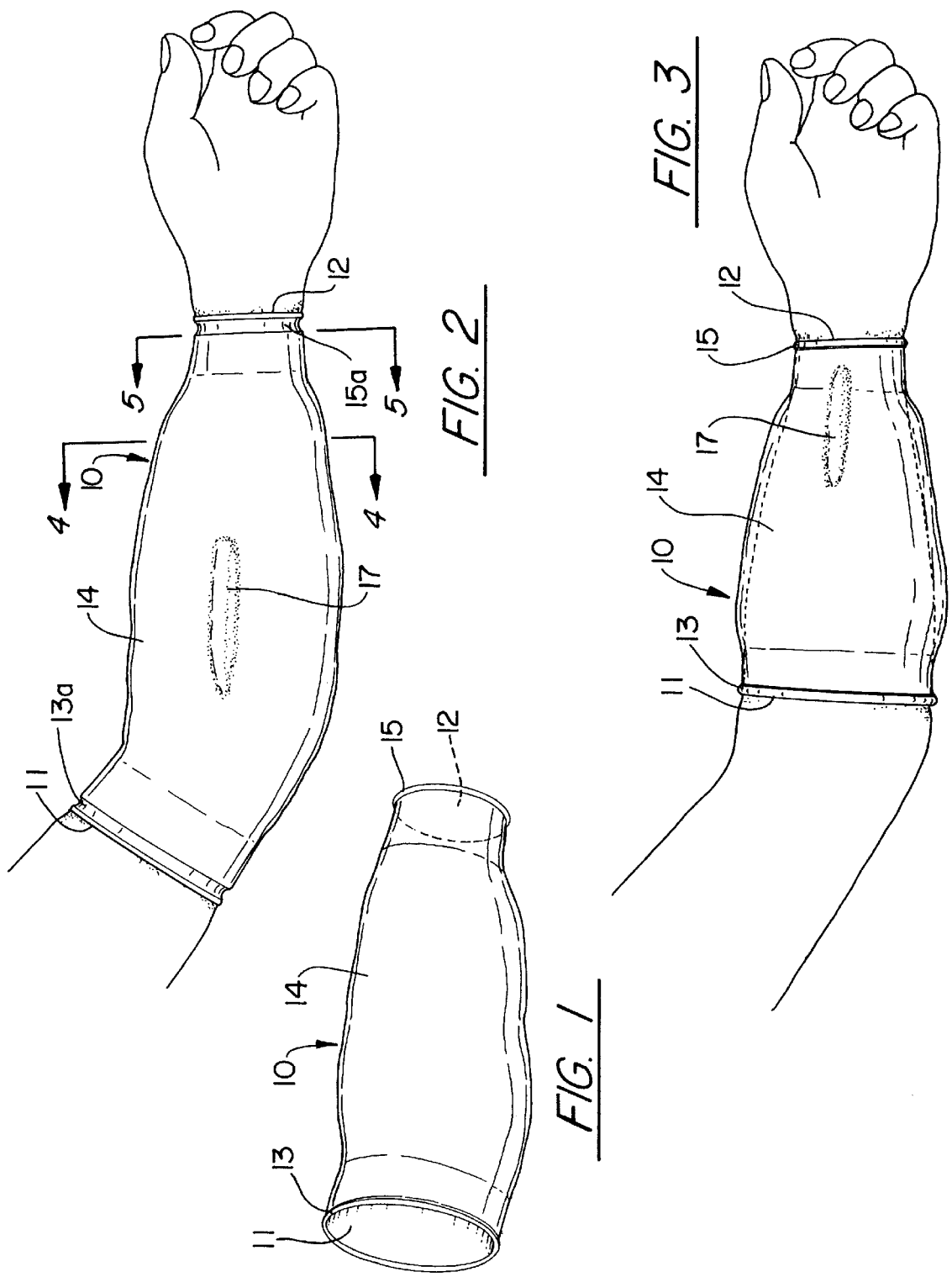

PROTECTIVE SLEEVE FOR A CHRONICALLY IMPLANTED INTRAVENOUS SITE

This is a continuation of U.S. Pat. Ser. No. 08/756,330 filed Nov. 26, 1996, now abandoned.

FIELD OF THE INVENTION

The present invention relates to a protective sleeve for a chronically-implanted intravenous (IV) site. It is constructed of a prophylactic waterproof material which prevents moisture from infiltrating the IV site.

BACKGROUND OF THE INVENTION

Many patients during hospital stays or other medical treatments require nutrients and/or drugs to be administered via an intravenous (IV) procedure. Usually an IV catheter is inserted into a vein in the patient's forearm or leg and then connected to a setup consisting of catheter tubing, IV tubing, and an IV bag containing a solution of nutrients and/or drugs. After the administration of the IV solution, if the patient does not need more solution, or will not need more solution for quite some time, the IV catheter maybe removed from the patient. If the patient thereafter requires more IV solution, a new IV catheter is inserted. If the patient requires more solution immediately, another bag is connected to the IV tubing.

The cost of medical care in general, and the hospital care in particular, has increased substantially in recent years. Because of this increase in cost, many hospitals now send patients home earlier than in years past. In some instances, these patients are sent home to further recover from their illness or injury, and may be attended to by either live-in or part time nurses. The growing tendency of hospitals to discharge patients earlier than in years past has lead to changes in IV procedures.

Specifically, in connection with an early hospital release, a patient may be sent home with a chronically-implanted IV site. A chronically implanted IV site consists of a catheter and its associated catheter tubing which is left implanted in the patient's vein, but which is capped off with a plug and a luer. Whenever a patient is in need of nutrients or drugs, a nurse can remove the plug and luer, and then attach IV tubing and an IV bag to the IV site. This procedure can be done at the patient's home, at an infusion center on outpatient basis, at a nursing home, at an AIDS treatment center, or at a hospice.

One problem however with a chronically-implanted IV site is that any moisture collecting around the IV site may act as a medium for the ingress of bacteria into the patient through the break in the skin where the IV catheter enters a vein. Consequently, an IV site must be protected during exposure to moisture making bathing inconvenient. In fact, showering is, as a practical matter, not permitted when a patient is provided with an implanted IV site.

Because infection of the IV site will lead to costly additional medical treatment, the protection of the site from moisture and subsequent infection is a powerful economic incentive.

OBJECT OF THE INVENTION

It is an object of the present invention to protect a chronically-implanted intravenous (IV) site (or other hazardous site on the arm or leg needing protection from moisture or infection) from exposure to moisture and infection.

It is another object of the invention to protect such a chronically-implanted IV site or other hazardous site from moisture with a sleeve-like covering that the patient can place on his arm without any assistance from a third party.

It is another object of the invention to protect such an IV site from moisture without dragging, snagging, pulling or otherwise interfering with the IV site.

It is yet another object of the invention to protect such an IV site or other hazardous site from exposure to moisture during showering.

A feature of this invention is that the sleeve is made from a single piece of latex material that is smooth on the inner and outer surface, includes an opening in the fore and aft ends and a means for providing a seal that tightly fits against the skin of the patient at In one embodiment a bead is located at each end which requires a rolling of the end to form the bead. In another embodiment an indentation is formed adjacent the aft and fore ends and the indentation which is an annular groove molded directly on the sleeve body. A plurality of spaced indentations at one end that is tapered may be included so that the patient can cut between indentations to size the sleeve to that particular patient.

SUMMARY OF THE INVENTION

The present invention comprises a protective sleeve for a chronically-implanted intravenous (IV) site or other hazardous site needing protection from moisture or infection. Such an IV site is usually located in the arm, but can also be located in the leg. The sleeve is constructed of a prophylactic waterproof material, and it protects the IV site from moisture when the IV tube is disconnected from the IV site, particularly during bathing, swimming or showering. Protecting a chronically-implanted IV site from moisture is essential because moisture which collects around an IV site can serve as a medium for bacteria to enter through the break in the skin caused by an IV catheter entering the vein.

The sleeve is pliable and cylindrical in shape with two open ends. The circumference of the sleeve is greater in the middle than on either end, and the circumference of one of the ends is normally greater than the other end. In one embodiment, the end with the larger circumference fits around the upper portion of a patient's arm and the end with the smaller circumference fits around the patient's forearm. The circumference of both ends are such that a gasket-like watertight seal is formed between the patient's arm and the sleeve. The shape of both ends of the sleeve is preferably formed in one embodiment of this invention by circular beads constructed from the same or similar prophylactic material as is used for the body of the sleeve. Instead of beads, the ends of the sleeve could be formed by a thickening of the sleeve material or by an indentation in the sleeve near each end opening of the sleeve.

The larger circumference of the middle portion of the protective sleeve causes it to be baggy or billowy when worn by a patient. This bagginess creates a dead air space around the IV site and prevents the sleeve from snagging, dragging or otherwise interfering with the implanted IV catheter, especially during the donning of the sleeve.

Before the IV site is exposed to moisture, such as during showering, the sleeve is placed over the IV site thereby protecting it from moisture. The end with the larger circumference allows the patient to easily slip his hand into the sleeve. The patient then moves the sleeve over the implanted site and the elbow, and up to the upper arm where the watertight seal is formed. Since only one hand can be used to don the sleeve, the elasticity of the beads allows the patient to use the underside of his arm as a stretch point, while placing his free hand on the opposite side of the bead and using that as another stretch point. The sleeve can then be moved up the arm by oscillating the stretch point formed by the free hand over an arc. The opposite end of the sleeve is likewise easily drawn over the hand and positioned on the forearm of the patient.

In another embodiment where the water-tight seal is formed by indentations or banding, at the reduced circumferential end adjacent the wrist, for example, a plurality of indentations axially spaced along a tapering or reduced circumference for in situ sizing the sleeve to fit the patient. In the preferred embodiment the thickness of the sleeve throughout is constant except in the bead configuration where the bead is made thicker than the remaining body portion.

BRIEF DESCRIPTION OF THE DRAWING

FIG. 1 is a perspective view of the present invention with a beaded water-tight seal configuration;

FIG. 2 is another perspective view of the invention positioned over the elbow of a patient with an indentation water-tight seal configuration;

FIG. 3 is another perspective view of the invention positioned over the forearm of a patient;

DETAILED DESCRIPTION OF THE PREFERRED EMBODIMENTS

Figure 4:
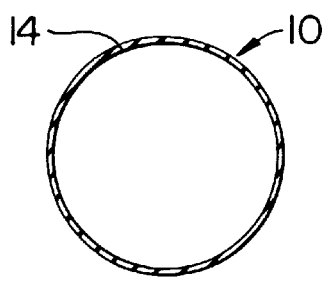
FIG. 4 is a sectional view taken over line 4—4 of FIG. 2.

FIG. 1 illustrates a protective sleeve 10 for a chronically-implanted intravenous (IV) site. Such an IV site is usually located in the forearm, but it can also be located in the patient's leg. The sleeve 10 is comprised of a body 14 which is constructed of a prophylactic waterproof material, preferably latex. The body 14 of the sleeve 10 is also preferably made from an elastomeric material. The sleeve 10 has an open end 11 and an open end 12. The circumference of open end 11 is preferably greater than the circumference of open end 12. The open ends 11 and 12 are each formed by elastomeric beads 13 and 15 respectively, and when placed around the patient's arm, the beads 13 and 15 form a gasket-like watertight seal around the patient's arm. The sleeve is formed from a single sheet that is molded with a bulbous portion intermediate the ends 11 and 12 so that the sleeve does not interfere with the IV and provide comfort to the patient. FIGS. 2 and 3 illustrate the positioning of the sleeve 10 over an IV site 17. In FIG. 2, the sleeve 10 is positioned over a patient's elbow, and in FIG. 3, the sleeve 10 is positioned over a patient's forearm.

As mentioned above, the body 14 of the sleeve 10 has a greater circumference in the middle than at the open ends 11 and 12, i.e. it billows in the middle. This creates a baggy dead air space between the body 14 of the sleeve 10 and the patient's arm. This bagginess prevents the IV site 17 from being snagged, dragged, pulled, compressed or otherwise disturbed, especially when the patient dons the sleeve 10.

Since the IV site 17 is normally located in a patient's arm, that patient only has one free hand to don sleeve 10. Therefore, the sleeve 10 is constructed in such a way so as to allow a patient with a chronically-implanted IV catheter to place the sleeve 10 onto his arm without assistance from a third party. With the IV tube disconnected from the catheter of the IV site, the patient slips his arm into the larger opening 11, and slides the sleeve 10 up his arm, over the IV site 17 and his elbow, and up to his upper arm. In particular, a patient slides the sleeve 10 up his arm by using the under portion of his arm as a fulcrum, pulling on the bead 13 on the opposite (upper) side of the arm, and moving his hand which is holding the bead 13 back and forth over a limited arc, thereby working the sleeve 10 up his arm. As the patient works the sleeve 10 up his arm, the body 14 will not snag the IV catheter since there is dead air space between the billowy middle portion of the body 14 and the IV site 17. When the bead 13 is moved above the elbow and positioned around the patient's upper arm, it forms a watertight seal around the upper arm. While placing the bead 13 in its proper place on the upper arm, the patient simultaneously places his hand through the smaller opening 12. The smaller open end 12 can then similarly be worked up the forearm, and the bead 15 forms a watertight seal around the forearm. When the sleeve 10 is in place, the watertight seals between the patient's arm and the beads 13 and 15 prevent the intrusion of water into the dead space area formed between the body 14 of the sleeve 10 and the patient's arm. The dead space area also prevents the sleeve 10 from unduly interfering with the IV site 17.

An IV site normally comprises a catheter having a distal end located in the patient's vein and a proximate end connectable to IV tubing. The catheter is normally one of two types—a peripheral line or a peripherally inserted central line (PICC). A peripheral line is 1–2 inches long, and a PICC is 18–26 inches long. The longer central line is typically wound around the patient's arm a few times to reduce the length of the exposed catheter. Consequently, if the patient has a peripheral line, the forearm needs to be covered by the sleeve 10 from the central portion of the wrist to just before the elbow. If the patient has a central line, the forearm needs to be covered a few inches peripheral to the elbow, and the upper arm needs to be covered approximately halfway up the upper arm (See FIG. 2). In either case, the overall length of the sleeve 10 will be approximately 11 inches, and the circumference range that each end will need in order to form a watertight seal will be 5–7 inches at the wrist end and 7–11 inches at the upper arm end. The length of the sleeve 10 and the circumference of the open ends 11 and 12 can be altered to fit different sized arms. Although the invention has heretofore been described as having open ends of unequal circumference, the open ends 11 and 12 can also be of equal circumference.

FIG. 3 illustrates an alternative embodiment of the invention. In this embodiment, the circumference of openings 11 and 12 are smaller so that a tight fit is achieved around the smaller portions of the forearm. As with other embodiments of the invention, the exact size of the openings depends upon the size of the patient's arm.

The present invention can also be used to protect other sites on the arm or leg requiring protection from moisture or infection, such as stitches, cuts, skin disease or any other hazardous site requiring protection from moisture or infection.

Figure 5:
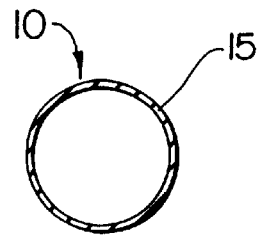
FIG. 5 is a sectional view taken along lines 5—5 of FIG. 2.

The sleeve 10 preferably is made from a latex and molded into a single unit to form the billowed portion and tapered ends 11 and 12. In one embodiment beads are formed at the ends 11 and 12 as illustrated in FIGS. 1 and 3. In the other embodiment the indentations 13a and 15a (the subscript "a" is used where parts in the various embodiments are similar)

serve to form the water tight seal. The indentations are formed in the mold. In this embodiment the thickness of the sleeve is constant throughout. This is illustrated by FIGS. 4 and 5 where a section is taken through the main body of the sleeve and a section is taken through the indentation. It being noted that the sleeve is smooth on both the inner and outer diameter.

Figure 6:
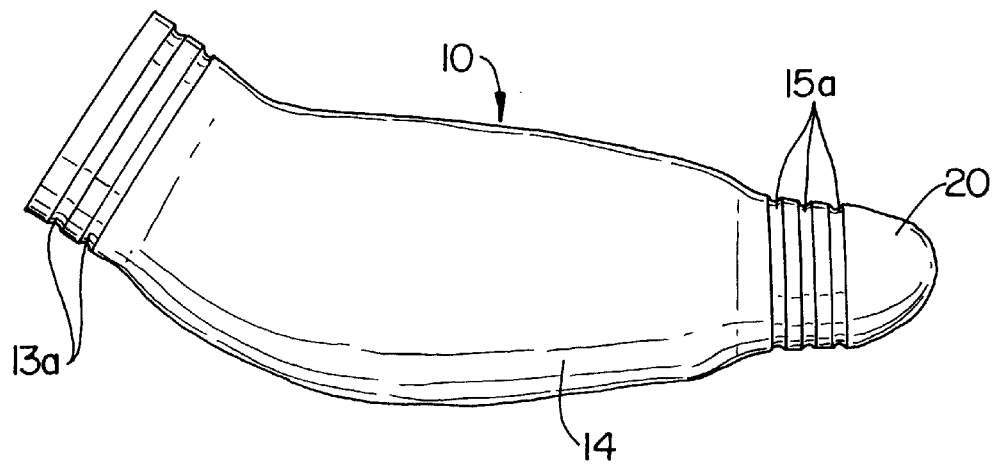
FIG. 6 is a partial view in perspective of this invention illustrating the banding at the reduced diameter end which allows the patient to cut the end of the sleeve between bands to obtain the desired fit.

FIG. 6 exemplifies another embodiment of this invention and is similar to the banding depicted in the embodiment of FIG. 2. A plurality of banding 15a is formed at the reduced circumference end and these indentations become progressively smaller so that the sleeve can be fitted to the individual patient. This graduated banding allows the patient to put the sleeve on and where the banding becomes tight enough to form a water-tight seal the remaining end portion would be cut-off. For example for a patient with a larger wrist the band may be water tight at the most aft indentation 15a and the remaining portion would be cut in situ or marked and then cut. In a patient that is smaller in size the indentation 15a may occur at the end and no cutting will occur.

In the manufacturing of the sleeve the mold is such that the main body is molded with an open end that fits over the mold and the opposite end 20 may be closed. This end is tapered as shown in FIG. 6 where a plurality of axially spaced indentations 15a are located. Obviously, the sleeve can be placed on the patient as described above and the smaller diameter end is cut off at the junction point where the indentation fits the limb with sufficient force to form the water-tight seal.

While the invention has been described in term of the aforementioned embodiments. Those skilled in the art will recognize that the invention can be practiced with modification within the spirit and cope of the appended claims.

It is claimed:

1. A protective sleeve for a hazardous site on an arm or leg comprising: a main body, said main body being comprised of a tube made from a single piece and having a constant thickness made from an elastomeric prophylactic waterproof material and having two open ends;
   a first portion of said main body to form a water-tight seal around a human limb at a first open end of a said tube;
   a second portion to form a water-tight seal with a human limb at a second end of said tube;
   the circumference of said main body being larger than the circumference at said first end and said second end so as to be sufficiently large enough to form a billowed portion when said sleeve is positioned on a human limb, thereby preventing said body portion from interfering with said intravenous site.

2. The protective sleeve as claimed in claim 1, including a first bead integrally formed at said first end and a second bead integrally formed at said second end.

3. The protective sleeve as claimed in claim 1, wherein said prophylactic waterproof material is latex.

4. The protective sleeve as claimed in claim 1 including a first annular indentation spaced adjacent to said first end and a second indentation spaced adjacent to said second end.

5. The protective sleeve as claimed in claim 4 wherein at least one of said first end or said second end is configured with a plurality of annular indentations are axially spaced and the main body where the annular indentations are located is tapered from intermediate said first end and said second end to a smaller diameter at the first end or the second end.

6. The protective sleeve as claimed in claim 5 wherein said first or second end is closed and the plurality of annular indentations are located at the closed end, wherein the closed end is cut-off when an indentation of said plurality of indentations forms a water-tight seal with respect to the limb of the patient.

7. A method for protecting a chronically-implanted intravenous site using protective sleeve of claim 6, comprising the steps of:
   i. placing an arm into said larger opening of said sleeve;
   ii. moving said sleeve up said arm by using the under portion of said arm as a fulcrum, grabbing one end of said one end by pulling on said one end with said free hand, and moving said one end over a limited arc to cover said site with said sleeve while IV tubing is disconnected from said site;
   iii. positioning the other end of said tube on a portion of said arm to cover said site with said sleeve, and
   iv. immersing said sleeve in water as by bathing or taking a shower with said protective sleeve covering said site.

8. The protective sleeve as claimed in claim 6, wherein said first open end is larger than said second open end permitting said first open to more easily form said watertight seal around an upper arm, and permitting said second open end to more easily form said watertight seal around a forearm.

9. The protective sleeve as claimed in claim 1, wherein said body sleeve is approximately 10 to 12 inches in length, said first open end is approximately 7 to 11 inches in circumference, and said second open end is approximately 5 to 7 inches in circumference.

10. The protective sleeve as claimed in claim 1 including at least one indentation at one end of said main body.

11. A method for protecting a chronically-implanted intravenous site using protective sleeve having annular indentations for forming a water tight seal with the limb of the patient, comprising the steps of:
   i. providing a protective sleeve made from a latex material formed in a tube with a constant thickness opened at either end and one end being larger than the other end and formed with a billowed portion intermediate the ends for loosely fitting over the chronically-implanted intravenous site;
   ii. placing an arm into the larger opening of the sleeve;
   iii. moving said sleeve up the arm by using the under portion of the arm as a fulcrum, grabbing one end of the tube opposite the fulcrum with the free hand, stretching the one end by pulling on said one end with the free hand, and moving the one end over a limited arc to cover said site with said sleeve while a IV tubing is disconnected from said site;
   iv. positioning the other end of said tube on a portion of said arm to cover said site with said sleeve; and
   v. immersing said sleeve in water by taking a shower or bathing with said protective sleeve covering said site.

* * * * *